United States Patent [19]

Hickham

[11] Patent Number: 5,037,298

[45] Date of Patent: Aug. 6, 1991

[54] APPARATUS AND IMPROVED PROCESS FOR REMOVING SALIVA WHILE RETRACTING CHEEKS AND LIPS

[76] Inventor: John J. Hickham, 2308 Houma Blvd., Apt. 825, Metairie, La. 70001

[21] Appl. No.: 71,488

[22] Filed: Jul. 9, 1987

Related U.S. Application Data

[63] Continuation-in-part of Ser. No. 801,413, Nov. 25, 1985, abandoned.

[51] Int. Cl.$^5$ ............................................. A61C 17/10
[52] U.S. Cl. ..................................................... 433/93
[58] Field of Search ................. 433/93, 140, 141, 136, 433/139; 128/12, 13

[56] References Cited

U.S. PATENT DOCUMENTS 3,049,806 8/1962 Cofresi .................................. 433/93
4,511,329 4/1985 Diamond ............................. 433/140

Primary Examiner—Cary E. Stone
Attorney, Agent, or Firm—John Wade Carpenter

[57] ABSTRACT

Apparatus for ejecting saliva and retracting cheeks and lips comprising a tongue retractor terminating into a pair of ends. A pair of saliva ejector is secured to the tongue retractor. A tongue retainer is attached to the tongue retractor, and a cheek and lip retractor is connected to the tongue retainer. A process for removing saliva from an oral cavity having a tongue and partially surrounded by cheeks and lips including expanding the cheeks and lips of the oral cavity with a cheek and lip retractor. The process additonally comprises retracting the tongue within the oral cavity with a tongue retractor that is supported by the base of the oral cavity, retaining the tongue in a generally fixed position and removing saliva along a structural portion of the tongue retractor.

23 Claims, 8 Drawing Sheets

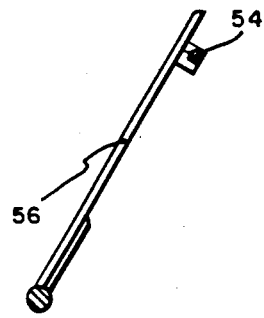
FIG. 3
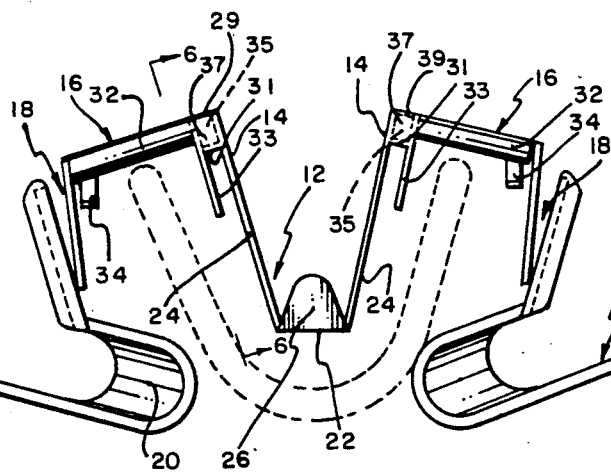
FIG. 4
FIG. 5
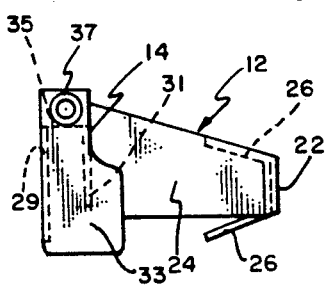
FIG. 6
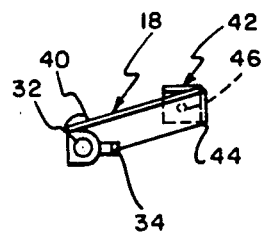
FIG. 7

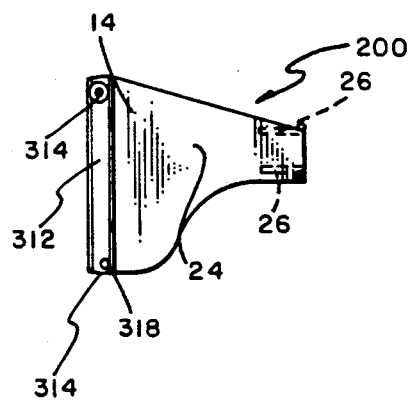
FIG. 19
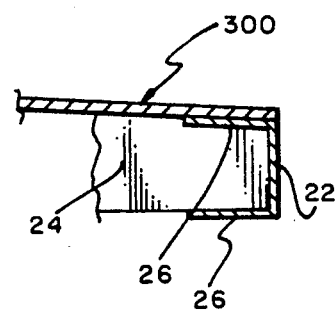
FIG. 18
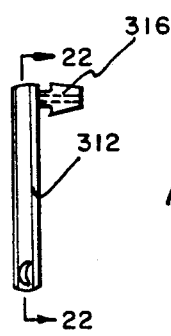
FIG. 21
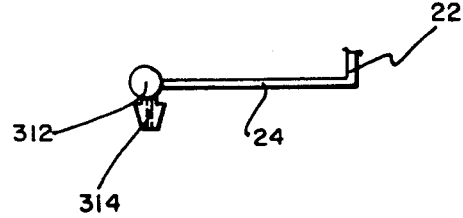
FIG. 20
FIG. 22
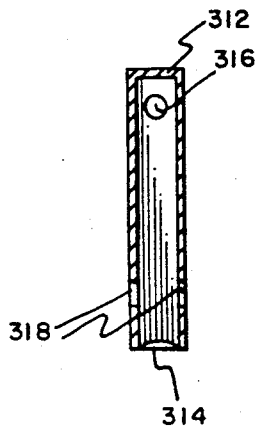
FIG. 23
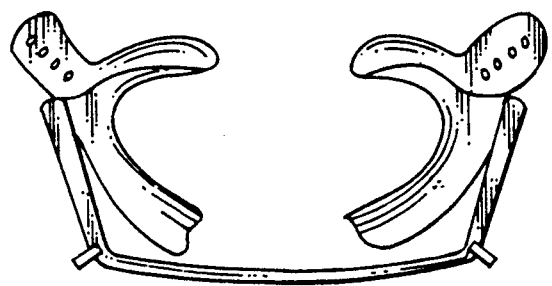

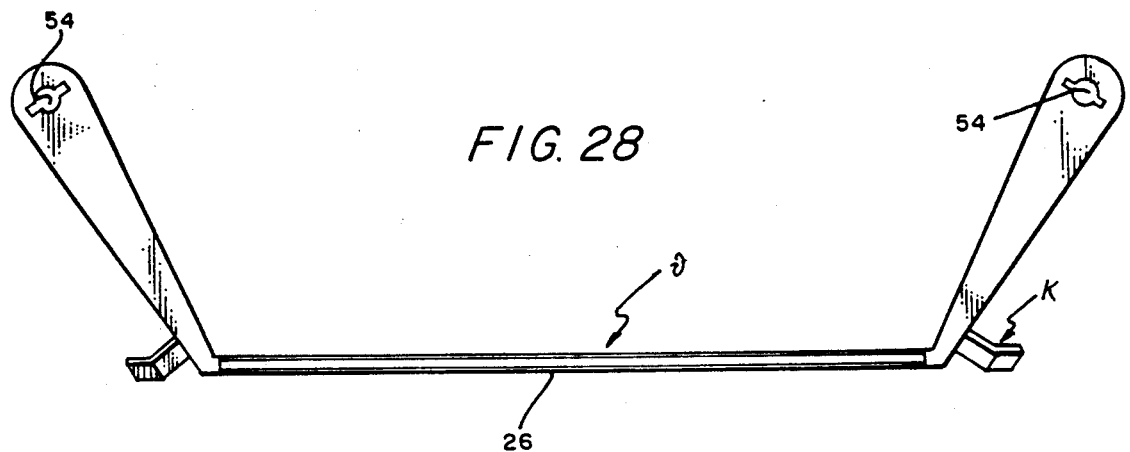
FIG. 28
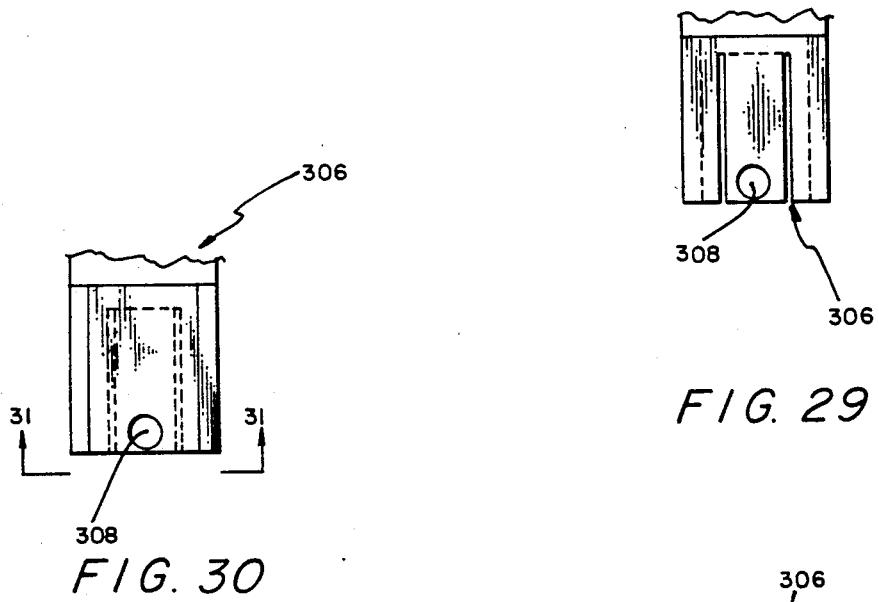
FIG. 29
FIG. 30
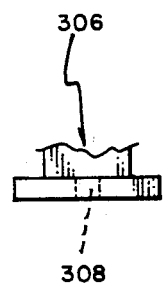
FIG. 31

APPARATUS AND IMPROVED PROCESS FOR REMOVING SALIVA WHILE RETRACTING CHEEKS AND LIPS

BACKGROUND OF THE INVENTION

This is a continuation-in-part application of my copending application Ser. No. 801,413 filed Nov. 25, 1985 abandoned.

1. Field of the Invention

This invention is related to a dental instrument. More specifically, this invention relates to an apparatus and process for removing saliva from an oral cavity while simultaneously retracting the cheeks and lips.

2. Description of the Prior Art

During dental procedures, the oral cavity is constantly being filled with body fluids, such as saliva. If these body fluids are not removed, these fluids adversely effect many of the dental procedures that require a dry field for success. The proximity of the oral soft tissues, such as the tongue, cheek and lip, to the field of work may make it difficult to perform those dental procedures also requiring a dry field. Therefore, the success of many operative dental procedures requires the removal of body fluids and soft tissues from the field of work.

There are other dental procedures in dentistry that require simultaneous preparation of the entire dental arch. These dental procedures may include extensive crown and bridge work; fluoride treatments; application of pit and fissure sealants; and the placement of orthodontic brackets using indirect bonding procedures.

Some conventional body fluid removal devices consist of tubing of various sizes and shapes that are connected at one end to a suction device and are opened at the opposite end for evacuation of the body fluids. These devices may often incorporate tissue shields to restrain soft tissue movement in the field of work, and generally pass over the teeth. These devices, as a rule, dry and isolate no more than a quarter of the dental arch.

Other conventional body fluid devices consist of a perforated metal tube that commences at the suction source, traverses the cheek side of the arch on one side, and curves back around the last tooth on that same side. The perforated metal tube also extends around the arch on the tongue side to the last tooth on the opposite side, around the last tooth on the same opposite side, and back up the arch on the cheek side to the suction source. There is a metal plate affixed to these devices which holds the tongue down. The devices do not adequately retract the soft tissue nor do they remove saliva from the floor of the mouth.

What is needed and what has been invented by me is an apparatus and process that does not include the foregoing deficiencies and satisfies any and all of the following: retracts the soft tissues (tongue, lip and cheek) from the field of work; exposes the entire oral arch with no part of the apparatus crossing over the tops of any teeth; comfortable for the patient; adequate suction to evacuate a constant flow of saliva and irrigation fluids; self-supporting; and restrains the tongue without hindering the act of swallowing which calls for the vertical movement of the tongue.

SUMMARY OF THE INVENTION

This invention broadly accomplishes its desired objects by providing an apparatus for ejecting saliva and retracting cheeks and lips comprising a generally V-shaped tongue retractor means including a cross-over plate, a first tongue shield plate pivotally secured to the cross-over plate, and a second tongue shield plate pivotally secured to the cross-over plate in an opposed relationship with respect to the first tongue shield plate. A tongue retainer means is secured to the cross-over plate and includes a first retainer arm and a second retainer arm that flare outwardly and away from each other. At least one saliva ejector means is secured to the generally V-shaped tongue retractor means; and a cheek and lip retractor means is connected to the first retainer arm and to the second retainer arm.

The invention further broadly accomplishes its desired objects by providing a process for removing saliva from an oral cavity means having a tongue and partially surrounded by cheeks and lips comprising the steps of:
(a) expanding the cheeks and lips of the oral cavity means with a pair of cheek and lip retractor means;
(b) retracting the tongue within the oral cavity means with a generally V-shaped tongue retractor means that is supported by the base of the oral cavity means and is open on an end for receiving a tongue therethrough when positioned in a mouth;
(c) retaining the tongue in a generally fixed position by a tongue retainer means that is mounted on top of said generally V-shaped tongue retractor means; and
(d) removing saliva along a structural position of said tongue retractor means.

Therefore, it is an object of the present invention to provide an apparatus and process for removing saliva while retracting cheeks and lips.

It is another object of this invention to provide an apparatus for removing saliva that retracts the soft tissues from the field of work and exposes the entire oral arch with no part of the apparatus crossing over the top of any teeth.

It is yet another object of this invention to provide an apparatus, for ejecting saliva and retracting cheeks and lips, that restrains the tongue without hindering the act of swallowing which calls for the vertical movement of the tongue.

These, together with various ancillary objects and features which will become apparent to those skilled in the art as the following description proceeds, are attained by this apparatus and process, a preferred embodiment being shown with reference to the accompanying drawings, by way of example only, wherein:

BRIEF DESCRIPTION OF THE DRAWINGS

FIG. 3 is a vertical sectional view taken in direction of the arrows and along the plane of line 3—3 in FIG. 4;

FIG. 4 is a front elevational view of the flexible member utilized to hold the pair of lip and cheek retractors;

FIG. 5 is a top plan view of another embodiment of the invention;

FIG. 6 is a vertical sectional view taken in direction of the arrows and along the plane of line 6—6 in FIG. 5;

FIG. 7 is a perspective view of the arms of the invention;

FIG. 18 is a vertical sectional view taken in direction of the arrows and along the plane of line 18—18 in FIG. 17;

FIG. 19 is a side elevational view of the tongue retractor;

FIG. 20 is a partial top plan view of the tongue retractor;

FIG. 21 is a side elevational view of the saliva conduit;

FIG. 22 is a vertical sectional view taken in direction of the arrows and along the plane of line 22—22 in FIG. 21;

FIG. 23 is a perspective view of the lip and cheek expander;

FIG. 28 is another embodiment of the flexible member;

FIG. 29 is a bottom plan view of the hinge;

FIG. 30 is a top plan view of the hinge; and

FIG. 31 is a vertical view taken in direction of the arrows and along the plane of line 31—31 in FIG. 30.

DETAILED DESCRIPTION OF THE INVENTION

Figure 1:
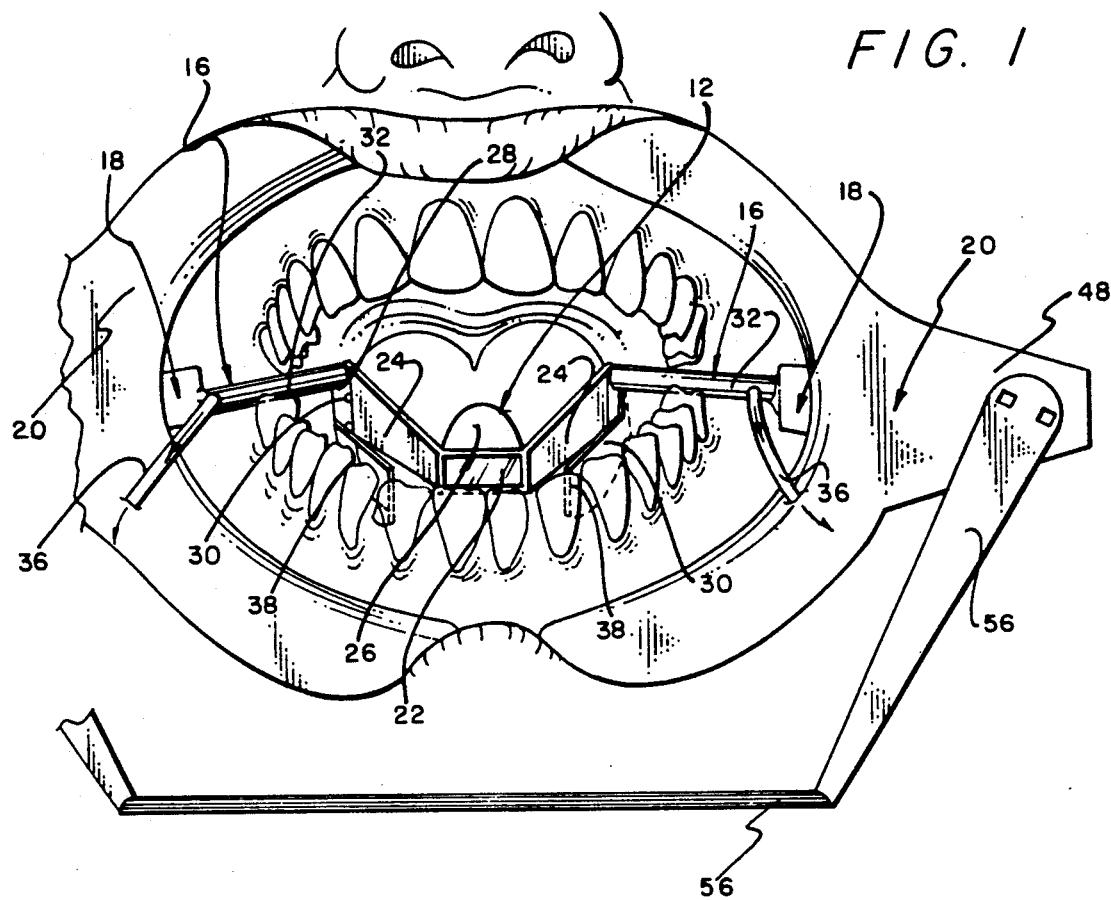
FIG. 1 is a perspective view of the invention inside an oral cavity with the lips and cheeks expanded.
Figure 2:
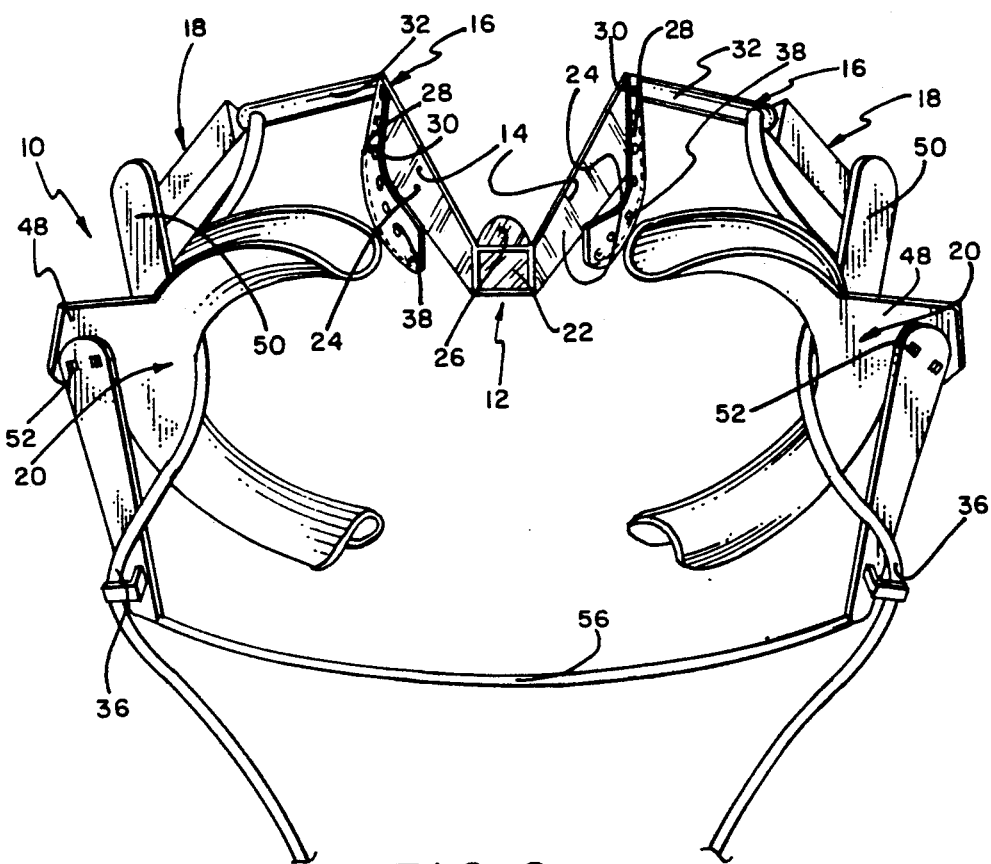
FIG. 2 is a perspective view of one embodiment of the invention.

Referring in detail now to FIGS. 1-11 of the drawings for illustration of one embodiment of the novel apparatus, wherein like or similar parts of the novel apparatus are identified by like reference numerals, there is seen in general the apparatus of this invention, generally illustrated as 10, for ejecting saliva and retracting cheeks and lips. Apparatus 10 includes a tongue retractor, generally illustrated as 12, which terminates into a pair of retractor ends 14—14. A pair of saliva ejectors, each generally illustrated as 16, is secured to the tongue retractor 12 as illustrated in FIG. 2; and a pair of arms, each generally illustrated at 18, attach respectively to the pair of saliva ejectors 16—16. The apparatus 10 also includes a pair of cheek and lip retractor, each generally illustrated as 20, connected respectively to the pair of arms 18—18.

The tongue retractor 12 has a generally V-shaped structure defined by a cross-over plate 22 and a pair of tongue shield plates 24—24 integrally bound to and on opposed sides of the cross-over plate 22. The tongue shield plates 24—24 terminate into the tongue retractor ends 14—14. The tongue retractor 12 additionally includes a pair of tongue guides 26—26 secured respectively to the top and the bottom of the cross-over plate 22 as illustrated in FIGS. 2 and 6. As also illustrated in FIG. 6, the tongue guide 26 attached to the bottom of the cross-over plate 22 diverges at an angle away from bottom plane of the cross-over plate 22 and the bottom plane of the tongue shield plates 24—24. The tongue guide secured to the top of the cross-over plane 22 is preferably disposed such as to be in the same plane as the top of the tongue shield plates 24—24.

The saliva ejectors 16—16 include various preferred embodiments. In one preferred embodiment (see FIGS. 1 and 2), each of the saliva ejectors 16—16 includes a tongue conduit 28 secured to and extending down its respective tongue retractor end 14. The pair of tongue conduits 28—28 each as a plurality of saliva apertures 30 for intaking of saliva and other body fluids. In another preferred embodiment for each of the saliva ejectors 16—16 (see FIGS. 5 and 6), a rear partition 29 and a front partition 31 extend down each of the two respective tongue retractor ends 14—14. A pair of guards 33—33 attaches respectively to partitions 29 and 31 positioned on both of the tongue retractor ends 14—14 to form an opening 35 (see FIGS. 5 and 6), defined by the partitions 29, 31, the guard 33, and the tongue retractor end 14, where through saliva and other body fluids travel upwardly from suction from a suction source. Each of the pair of openings 35—35 has a roof 57 in order that any suction from a suction source is confined to within the openings 35—35 and is not dissipated. Preferably, the rear partition 29 is larger than the front partition 31.

The saliva ejectors 16—16 also include a pair of cross-over saliva tubes 32—32 bound respectively in one embodiment to the pair of tongue conduits 28—28 (see FIGS. 1 and 2), and in another embodiment to the pair of guards 33—33 (see FIGS. 5 and 6). Each of the saliva tubes 32—32 has a saliva nozzle 34 which mates into s saliva suction hose 36 that has an internal pressure differential from a suction source in order that saliva and other body fluids may be sucked from the oral cavity, through the openings 35—35 in one embodiment, or the saliva apertures 30 of the tongue conduits 28—28 in the other embodiment, into and through the saliva tubes 32—32, out of the saliva nozzles 34—34, and through the saliva suction hoses 36—36 for eventual discharge.

In a preferred embodiment of one embodiment of the saliva ejectors 16—16, in order to protect the gums and other soft tissues, a pair of tissue shields 38—38 is bound respectively to the pair of tongue conduits 28—28 as illustrated in FIGS. 1 and 2.

Each arm 18 has a pair of arm ends designated respectively as 40 and generally as 42. Arm ends 40—40 pivotally attach respectively to the cross-over saliva tubes 32—32. Arm ends 42—42 terminate into generally T-shaped male fittings 44—44 having a structure respectively defining a pair of arm recesses 46—46 (see FIGS. 7 and 8).

The check and lip retractors 20—20 are preferably arcuate in shape, and each retractor 20 has a pair of lug ears designated as 48 and 50. Lug ears 48—48 have ear openings 52—52 which removable receive T-shaped protrusions 54—54 of a flexible resilient member 56, which is preferably spring loaded, and holds the cheek and lip retractor 20—20 apart in operation of the invention.

Figure 8:
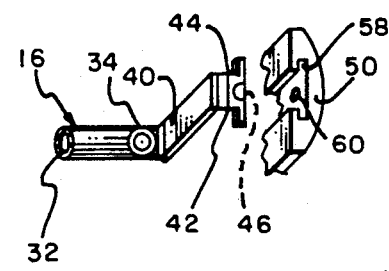
FIG. 8 is a partial perspective view of the arm and the lug ears.
Figure 9:
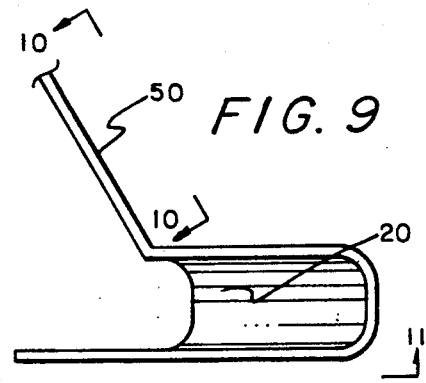
FIG. 9 is a top plan view of the lip and cheeks retractor.
Figure 10:
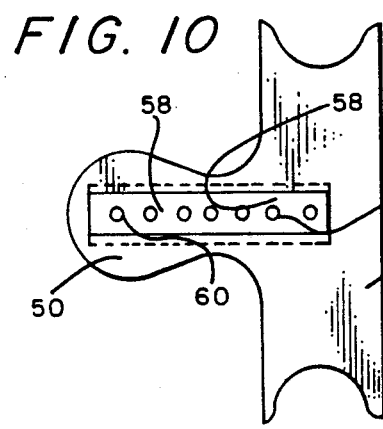
FIG. 10 is a partial front elevational view of the lip and cheek retractor taken in direction of the arrows and along the plane of line 10—10 in FIG. 9.
Figure 11:
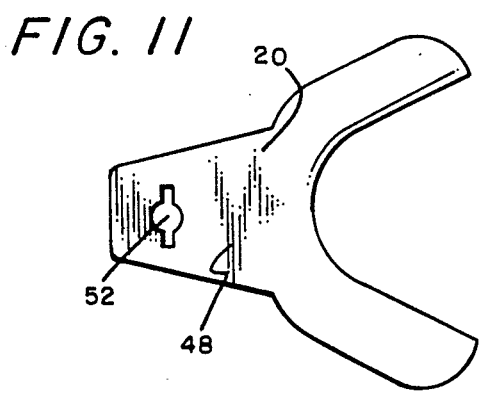
FIG. 11 is a front elevational view of the lip and cheek retractor taken in direction of the arrows and along the plane of line 11—11 in FIG. 9.

The lug ears 50—50 have a structure essentially defining generally T-shaped female channels 58—58 having a plurality of aligned protruding knobs 60 (see FIGS. 8 and 10). The T-shaped female channels 58—58 are sized and adapted to slidably receive and mate with the T-shaped male fittings 44—44. The mating process and adaptation includes the removable lodging of one of the protruding knobs 60 into the arm recesses 46—46 in order to removably affix the arms 18—18 to the cheek and lip retractors 20—20. The particular knob 60 along the female channels 58—58 which the arm recesses 46—46 are to receive depends on the size and shape of the user's mouth. A person with a large and/or deep mouth would use one of the knobs 60 within female channels 58—58 farthest away from the arcuate structure of the retractors 20—20 for connecting the arms 18—18 to the cheek and lip retractors 20—20. Obviously, the closer the T-shaped male fittings 44—44 are slid towards the arcuate structure of the retractors 20—20, the shorter the effective length of the arms 18—18 become. Stated broadly another way, the overall length of the apparatus 10 that goes into one's mouth is shortened.

With continuing reference to FIGS. 1-11 of the drawings for operation of one embodiment of the invention and the process for removing saliva from an oral cavity having a tongue and partially enclosed by cheeks and lips, the patient's mouth is opened and the tongue retractor 12 is positioned such that the tongue is confined to within the walls of the tongue shield plates 24—24 and the cross-over plate 22. The tongue guides 26—26 should be imposed over the top and bottom of the tip of the tongue to assist in guiding and retaining the tongue away from the field of work, especially when the patient has to swallow. The pair of saliva ejectors 16—16 should be positioned behind the last teeth of the lower teeth as illustrated in FIG. 1. The cheeks and lips of the patient's mouth are expanded with the pair of cheek and lip retractors 20-02, and held apart by attaching the T-shaped protrusion 54—54 of the flexible member 56 to within the ear openings 52—52 of the lug ears 48—48. Care is taken to ensure that the suction hoses 36—36 extend away from the nozzles 34—34 and have a source of suction.

When the source of suction is activated, saliva and other body fluids are removed from the base of the patient's mouth, through either the openings 35—35, or the saliva apertures 30 and along the tongue conduits 28—28. Openings 35—35 and tongue conduits 28—28 are both located at or to the tongue retractor ends 14—14. Continuous suction from the source of suction causes the saliva and other body fluids to pass out of the openings 35—35 or the tongue conduits 28—28, into and through the saliva tubes 32—32, out of the nozzles 34—34, and through the suction hoses themselves for eventual discard. The saliva and body fluids are removed between the tongue and gums of the patient which is in the area of maximum accumulation. In one embodiment of the saliva ejectors 16—16, the shields 38—38 separate the tongue conduits 28—28 from the gums, and generally protects the gums and other soft tissues.

Thus, the invention in FIGS. 1-11 provides an apparatus 10 and process for removing saliva and other body fluids, while retracting cheeks and lips and other soft tissues from the field of work, and exposes the entire oral arch with no part of the apparatus 10 crossing over the top of any teeth.

Referring in detail now to FIGS. 12-31 for another embodiment of the invention, there is seen a generally V-shaped tongue retractor, generally illustrated as 200, having the cross-over plate 22 and the pair of tongue shield plates 24—24 pivotally secured on opposed sides of the cross-over plate 22. The tongue shield plates 24—24 terminate into the tongue retractor 14—14. The tongue retractor 200 additionally includes the pair of tongue guides 26—26 secured respectively to the top and bottom of the cross-over plate 22.

A tongue retainer, generally illustrated as 300, is secured to the cross-over plate 22 as illustrated in FIG. 18. The tongue retainer 300 is also secured to the guide 26 mounted to the top of the cross-over plate 22 as further illustrated in FIG. 18. It should be understood that the tongue retainer 300 is not connected to the pair of tongue shield plates 24—24. The reason for this is that it is highly desirable that each of the tongue shield plates 24 can pivot in direction of the arrows in FIGS. 14-16 in order to be able to accommodate various tongue and mouth sizes.

Figure 16:
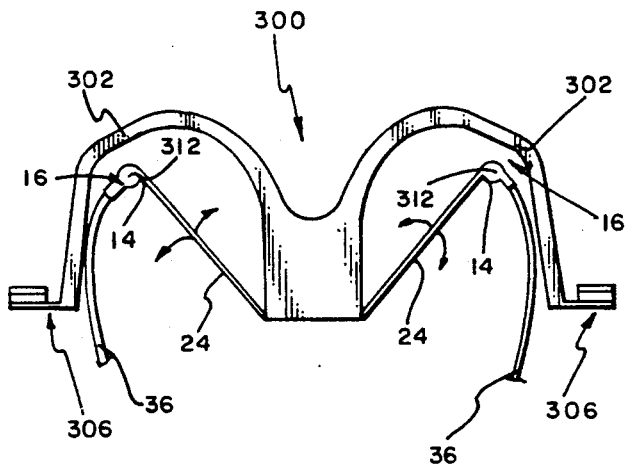
FIG. 16 is a partial top plan view of the invention in FIG. 15.
Figure 17:
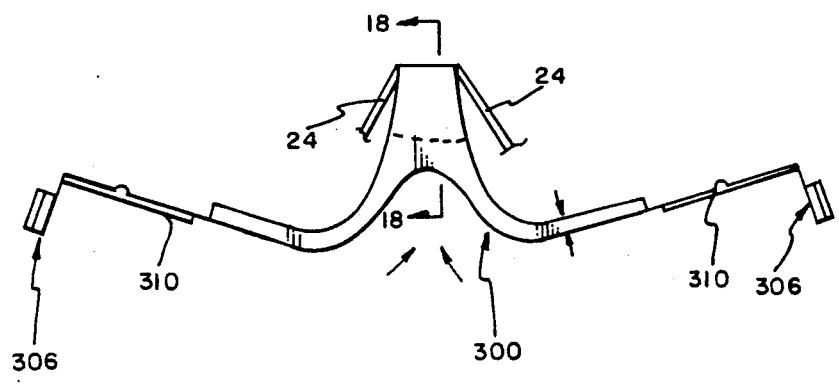
FIG. 17 is a partial top plan view of the invention in FIG. 14.
Figure 24:
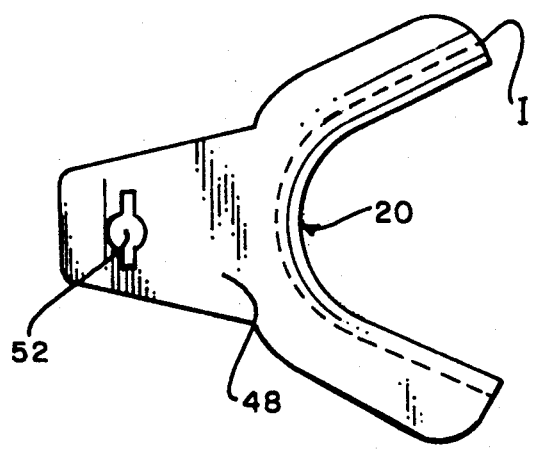
FIG. 24 is a front elevational view of the lip and cheek retractor of FIG. 11.

There are two embodiments of the tongue retainer 300. In one embodiment (see FIGS. 15 and 16), the tongue retainer 300 is generally M-shaped and comprises a pair of U-shaped arms 302—302, as illustrated in FIG. 16. In this embodiment, the U-shaped arms 302—302 are each integral or generally one solid piece, and flare outwardly and away from each other. A retaining post 304 is secured to each of the arms 302—302, and functions to assist in keeping the saliva suction hoses 36—36 away from the area of work (see FIGS. 12 and 13). At the end of each of the U-shaped arms 302—302 is a generally T-shaped hinge member, generally illustrated as 306 (see FIGS. 29, 30 and 31), pivotally secured thereto. Each hinge member 306 has an aperture 308 wherethrough one of the protruding knobs 60 (of T-shaped female channels 58—58) can removably lodge and mate with the aperture 308.

Figure 12:
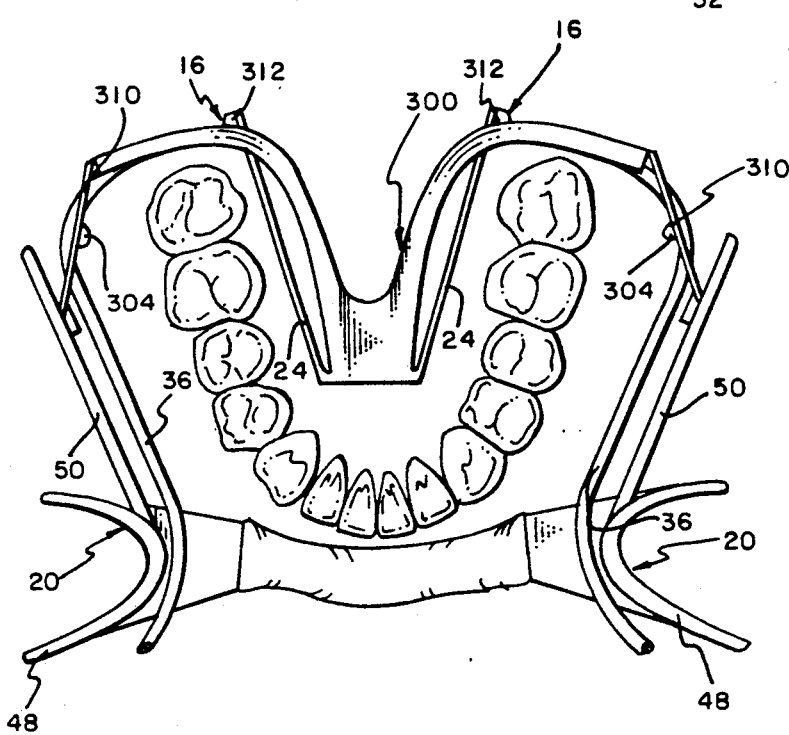
FIG. 12 is a top plan view of another embodiment of the invention.
Figure 13:
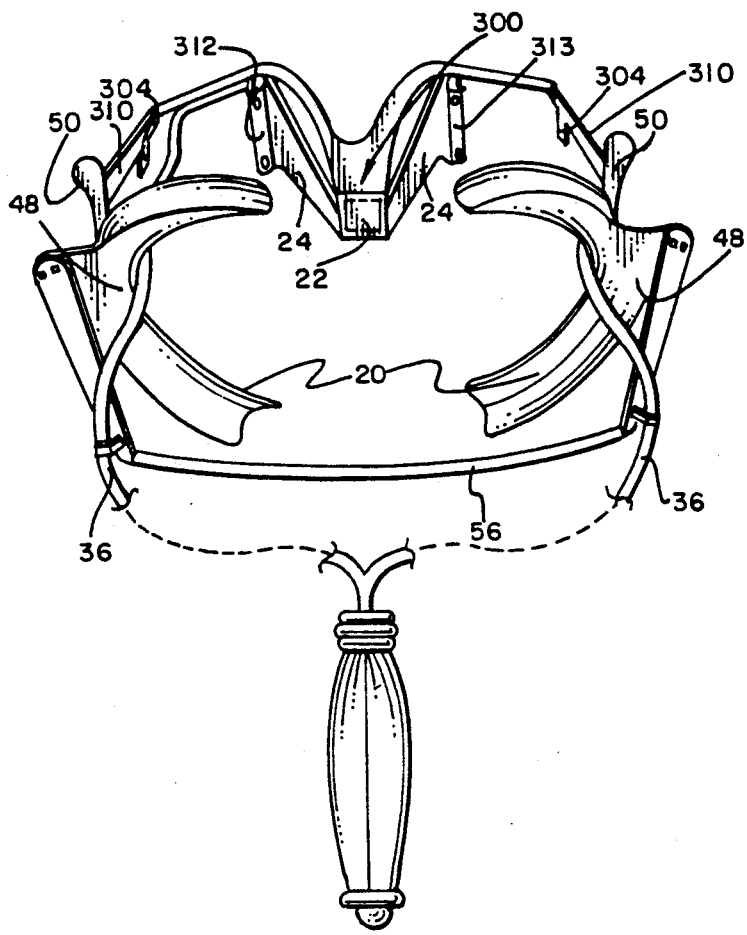
FIG. 13 is a perspective view of the invention in FIG. 12.
Figure 14:
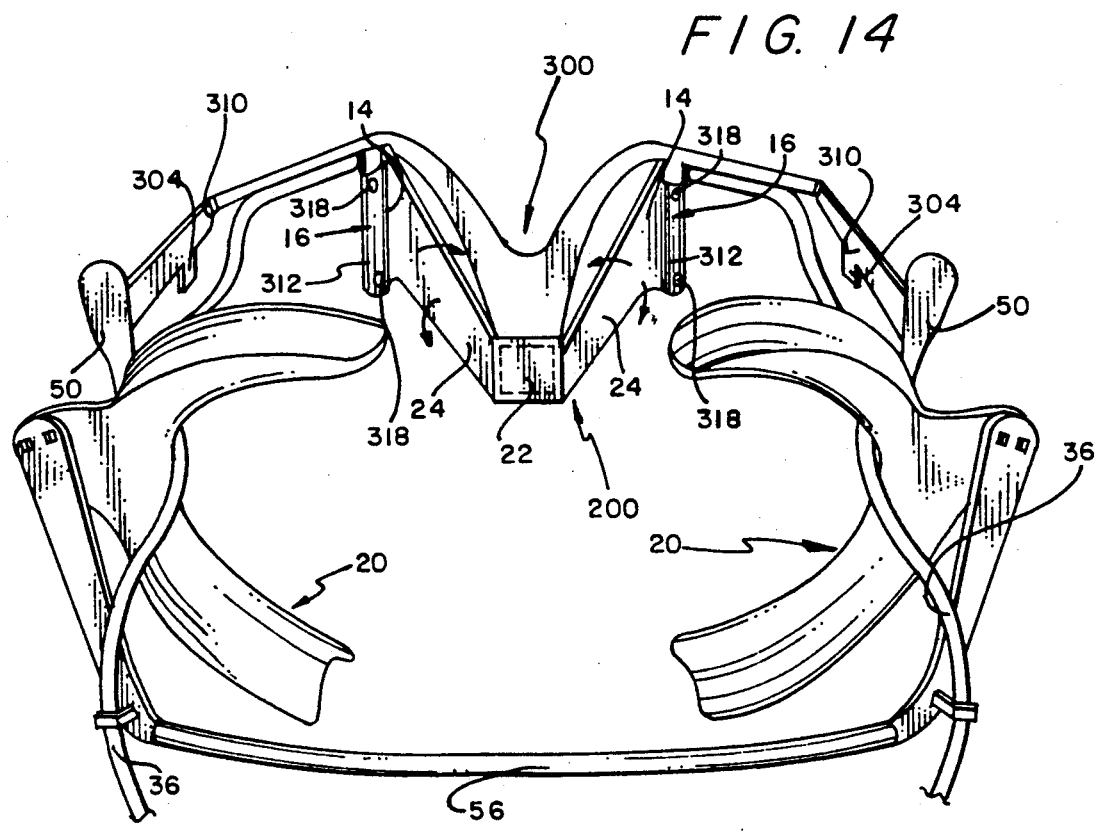
FIG. 14 is an exploded perspective view of the invention in FIG. 12.
Figure 15:
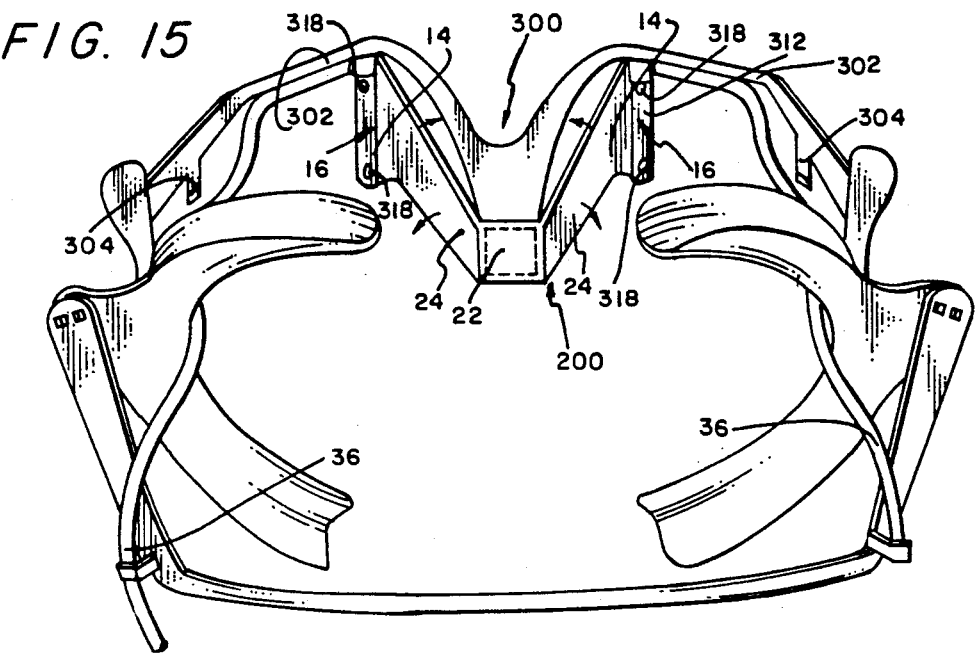
FIG. 15 is an exploded perspective view of yet another embodiment of the invention in FIG. 12.

In another embodiment of the tongue retainer 300 (see FIGS. 12, 13, 14 and 17), the tongue retainer 300 is generally Y-shaped. Arms 310—310 are respectively secured pivotally or flexibly to the Y-shaped retainer 300 as illustrated in FIGS. 12 and 14. Retaining posts 304—304 respectively connect to the pair of arms 310—310. The generally T-shaped hinge member 306 is secured pivotally to the end of each of the arms 310—310.

The saliva ejectors 16—16 for the embodiments of the invention in FIGS. 12, 13 and 14, and FIGS. 15 and 16, each include a saliva conduit 312 integrally attached to each of the tongue shield plates 24, more specifically attached to and extending along each of the retractor ends 14 of each of the tongue shield plates 24. Each saliva conduit 312 has an inlet 314, an outlet 316 to which suction hose 36 attaches, and apertures 318.

The pair of cheek and lip retractors 20—20 are secured to the arms 310—310, or to the retainer arms 302—302, through the hinge member 306 (or any other type of flexible fastening means) which is similar to T-shaped male fittings 44—44.

The cheek and lip retractors 20—20 are preferably arcuate in shape, and each retractor 20 has the pair of lug ears which were designated as 48 and 50. Lug ears 48—48 have the ear openings 52—52 which removably receive the T-shaped protrusions 54—54 of the flexible resilient member 56, which is preferably spring loaded, and holds the cheek and lip retractor 20—20 apart in operation of the invention.

Figure 25:
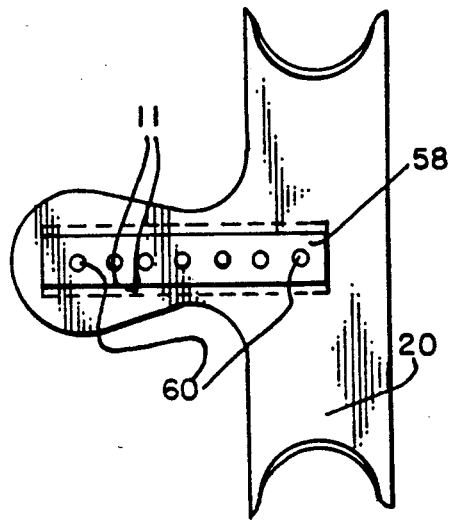
FIG. 25 is the retractor of FIG. 10.
Figure 26:
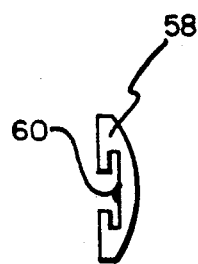
FIG. 26 is a vertical sectional view taken in direction of the arrows and along the plane of line 26—26 in FIG. 25.
Figure 27:
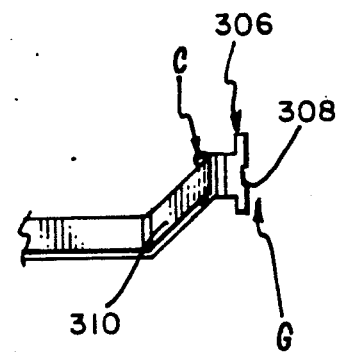
FIG. 27 is a partial view of the retainer arm having a hinge mounted at the end.

The lug ears 50—50 have a structure essentially defining generally the T-shaped female channels 58—58 having the plurality of aligned protruding knobs 60 (see FIGS. 25 and 26). The T-shaped female channels 58—58 are sized and adapted to slidably receive and mate with the T-shaped hinges 44—44. The mating process and adaptation includes the removable lodging of one of the protruding knobs 60 into the arm recesses 308 in order to removably affix the arms 310—310 (or the retainer 300) to the cheek and lip retractors 20—20. The particular knob 60 along the female channels 58—58 which the recesses 308 are to receive depends on the size and shape of the user's mouth as was previously indicated.

With continuing reference to FIGS. 12-31 of the drawings for operation of the other embodiment of the invention and the process for removing saliva from an oral cavity having a tongue and partially enclosed by cheeks and lips, the patient's mouth is opened and the tongue retractor 12 is positioned such that the tongue is confined to within the walls of the tongue shield plates 24—24 and the cross-over plate 22. The tongue guides 26—26 should be imposed over the top and bottom of the tip of the tongue to assist in guiding and retaining the tongue away from the field of work, especially when the patient has to swallow. The retainer 300 rests on top of the tongue to retain the tongue in a relatively fixed position. The pair of saliva ejectors 16—16 should be positioned behind the last teeth of the lower teeth as illustrated in FIG. 12. The cheeks and lips of the patient's mouth are expanded with the pair of cheek and lip retractors 20—20, and held apart by attaching the T-shaped protrusion 54—54 of the flexible member 56 to within the ear openings 52—52 of the lug ears 48—48. As indicated, care is taken to ensure that the suction hoses 36—36 extend away from the outlets 316—316 (or nozzles) and have a source of suction.

When the source of suction is activated, saliva and other body fluids are removed from the base of the patient's mouth, through the openings or apertures 318 and the inlet 314 of the saliva conduits 312—312. Conduits 312—312 are both located at or to the tongue retractor ends 14—14. Continuous suction from the source of suction causes the saliva and other body fluids to pass out of the outlets 316—316, and through the suction hoses 36—36 themselves for eventual discard. The saliva and body fluids are removed between the tongue and gums of the patient which is in the area of maximum accumulation.

While the present invention has been described herein with reference to particular embodiments thereof, a latitude of modification, various changes and substitutions are intended in the foregoing disclosure, and in some instances, some features of the invention will be employed without a corresponding use of other features without departing from the scope of the invention as set forth.

I claim:

1. An apparatus for ejecting saliva and retracting cheeks and lip means comprising a tongue retractor means including a cross-over plate means, a first tongue shield plate secured to said cross-over plate means, and a second tongue shield plate secured to the cross-over plate means in an opposed relationship with respect to the first tongue shield plate; a tongue retainer means secured to said cross-over plate means and including a first retainer arm and a second retainer arm that flare outwardly and away from each other; at least one saliva ejector means secured to said tongue retractor means; and a cheek and lip retractor means connected to said first retainer arm and to said second retainer arm.

2. The apparatus of claim 1 wherein said tongue retainer means is generally M-shaped.

3. The apparatus of claim 1 additionally comprising a first retaining post secured to said first retainer arm, and a second retaining post secured to said second retainer arm.

4. The apparatus of claim 3 wherein said first and said second retainer arm are each generally U-shaped.

5. The apparatus of claim 1 wherein said at least one saliva ejector means comprises a first saliva ejector means and a second saliva ejector means, said first saliva ejector means is secured to said first tongue shield plate, and said second saliva ejector means is secured to said second tongue shield plate.

6. The apparatus of claim 5 wherein said first saliva ejector means comprises a first saliva conduit integrally attached to said first tongue shield plate, and said second saliva ejector means comprises a second saliva conduit integrally attached to said second tongue shield plate.

7. The apparatus of claim 6 wherein said first saliva conduit comprises a first saliva inlet, a first saliva outlet, and a structure defining at least one first aperture.

8. The apparatus of claim 7 wherein said second saliva conduit comprises a second saliva inlet, a second saliva outlet, and a structure defining at least one second aperture.

9. The apparatus of claim 8 wherein said first tongue shield plate terminates in a first retractor end, said first saliva conduit is attached to and extends along said first retractor end; said second tongue shield plate terminates in a second retractor end, said second saliva conduit is attached to and extends along said second retractor end.

10. The apparatus of claim 1 additionally comprising an upper tongue guide attached to the top of the cross-over plate and a lower tongue guide connected to the bottom of the cross-over plate.

11. The apparatus of claim 10 wherein said tongue retainer means is additionally secured to said upper tongue guide.

12. The apparatus of claim 1 wherein said first tongue shield plate and said second tongue shield plate are respectively pivotally secured to said cross-over plate means such that said tongue retractor means can be formed into a generally V-shape.

13. An apparatus for ejecting saliva and retracting cheeks and lip means comprising a tongue retractor means including a cross-over plate means, a first tongue shield plate secured to said cross-over plate means, and a second tongue shield plate secured to the cross-over plate means in an opposed relationship with respect to the first tongue shield plate; a tongue retainer means secured to said cross-over plate means; a first arm secured to said tongue retainer means; a second arm secured to said tongue retainer means; at least one saliva ejector means secured to said tongue retractor means;

and a cheek and lip retractor means connected to said first arm and to said second arm.

14. The apparatus of claim 13 additionally comprising a first retaining post secured to said first arm, and a second retaining post secured to said second arm.

15. The apparatus of claim 13 wherein said at least one saliva ejector means comprises a first saliva ejector means and a second saliva ejector means, said first saliva ejector means is secured to said first tongue shield plate, and said second saliva ejector means is secured to said second tongue shield plate.

16. The apparatus of claim 15 wherein said first saliva ejector means comprises a first saliva conduit integrally attached to said first tongue shield plate, and said second saliva ejector means comprises a second saliva conduit integrally attached to said second tongue shield plate.

17. The apparatus of claim 16 wherein said first saliva conduit comprises a first saliva inlet, a first saliva outlet, and a structure defining at least one first aperture, and said second saliva conduit comprises a second saliva inlet, a second saliva outlet, and a structure defining at least one second aperture.

18. The apparatus of claim 17 wherein said first tongue shield plate terminates in a first retractor end, said first saliva conduit is attached to and extends along said first retractor end; said second tongue shield plate terminates in a second retractor end, said second saliva conduit is attached to and extends along said second retractor end.

19. The apparatus of claim 13 additionally comprising an upper tongue guide attached to the top of the cross-over plate and a lower tongue guide connected to the bottom of the cross-over plate, and said tongue retainer means is additionally secured to said upper tongue guide.

20. The apparatus of claim 13 wherein said first tongue shield plate and said second tongue shield plate are respectively pivotally secured to said cross-over plate means such that said tongue retractor means can be formed into a generally V-shape.

21. A process for removing saliva from an oral cavity means having a tongue and partially surrounded by cheeks and lips comprising the steps of:
  (a) expanding the cheeks and lips of the oral cavity means with a pair of cheek and lip retractor means;
  (b) retracting the tongue within the oral cavity means with a tongue retractor means that is supported by the base of the oral cavity means and is formed with a cross-over plate means and a pair of shield plates pivotally secured thereto for bordering a tongue when positioned in a mouth;
  (c) retaining the tongue in a generally fixed position by a tongue retainer means that is mounted on top of said cross-over plate means of said tongue retractor means; and
  (d) removing saliva along a structural position of said tongue retractor means.

22. The process of claim 21 additionally comprising guiding the tongue with a pair of superimposed spaced tongue guide means that are secured to said tongue retractor means.

23. An apparatus for ejecting saliva comprising a tongue retractor means including a cross-over plate means, a first tongue shield plate secured to said cross-over plate means, and a second tongue shield plate secured to the cross-over plate means in an opposed relationship with respect to the first tongue shield plate; a tongue retainer means secured to said cross-over plate and including a first retainer arm and a second retainer arm that flare outwardly and away from each other; and at least one saliva ejector means secured to said tongue retractor means.

* * * * *